United States Patent [19]

Renier

[11] 4,177,571

[45] Dec. 11, 1979

[54] OPHTHALMIC DEVICE FOR MEASURING VERTEX DISTANCE AND PANTOSCOPIC TILT ANGLE

[76] Inventor: Gary L. Renier, 3726 Fairway Rd., Fargo, N. Dak. 58102

[21] Appl. No.: 908,127

[22] Filed: May 22, 1978

[51] Int. Cl.² .............................................. A61B 3/10
[52] U.S. Cl. ................................... 33/200; 33/143 R; 33/174 D
[58] Field of Search ................ 33/200, 174 A, 174 D, 33/143 R, 143 C, 143 E, 147 K, 147 R, 143 M, 143 J, 141 K

[56] References Cited

U.S. PATENT DOCUMENTS

| | | | |
|---|---|---|---|
| 563,089 | 6/1896 | Strange | 33/143 M X |
| 724,963 | 4/1903 | Spaulding | 33/143 M |
| 758,283 | 4/1904 | Shaefer | 33/14 M |
| 1,238,045 | 8/1917 | Nelson | 33/143 M |
| 1,488,984 | 4/1924 | Heyne | 33/147 K |
| 2,694,262 | 11/1954 | Daniel | 33/143 M X |
| 3,995,373 | 12/1976 | Brumbelow | 33/143 M |

*Primary Examiner*—William D. Martin, Jr.
*Attorney, Agent, or Firm*—Dressler, Goldsmith, Clement, Gordon & Shore, Ltd.

[57] ABSTRACT

An ophthalmic measuring device for measuring vertex distance and pantoscopic tilt angle is disclosed. The device has a body and two arms which move slidably relative to each other to contact the eye and trial lens and a scale which measures the eye-lens distance. An implement for measuring the angle at which the spectacle temples are tilted relative to the frame front is also part of the device.

5 Claims, 4 Drawing Figures

U.S. Patent      Dec. 11, 1979      4,177,571
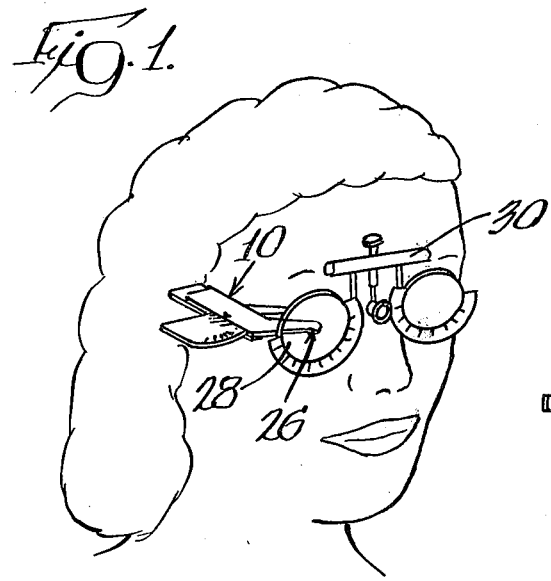
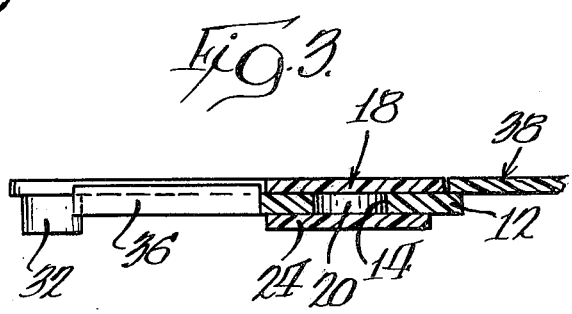
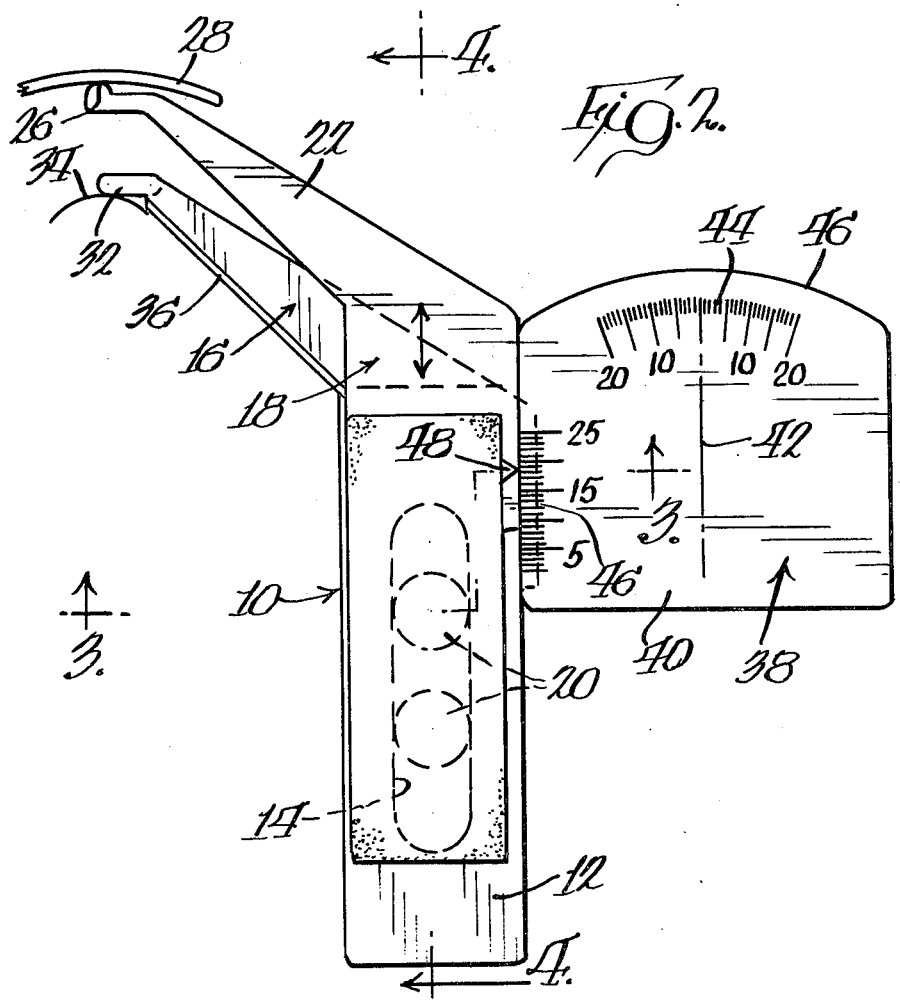
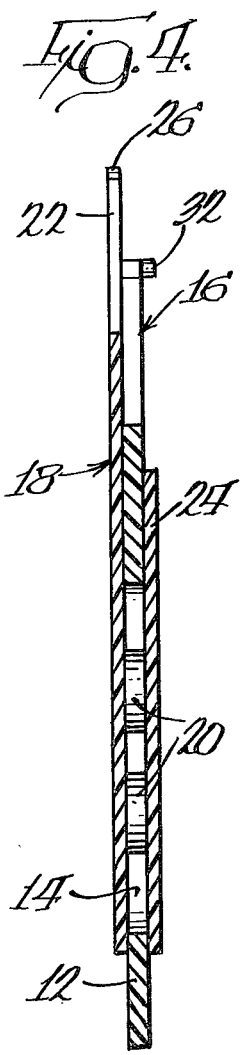

OPHTHALMIC DEVICE FOR MEASURING VERTEX DISTANCE AND PANTOSCOPIC TILT ANGLE

BACKGROUND OF THE INVENTION

Techniques for measuring ophthalmic refractions for patients who are aphakic or highly miopic are old in the art and have served refractionists for several years. After these refractions are obtained, however, the vertex distance—the distance between the optical center of the eye and the optical center of the posterior trial lens—and the pantoscopic tilt alteration—the angle at which the spectacle temples are moved off the frame front's perpendicular plane—must still be determined. These latter measurements have caused particular difficulties for refractionists with patients who are aphakic or highly miopic.

Thus, as can be seen from standard vertex conversion charts, a change or error of 1 mm. in the vertex distance can alter the prescription by 0.50 diopter, which results in the patient's having needlessly poor vision. Similarly, since the standard refracting plane of refracting glasses or trial frames is perpendicular to the visual axis while in use, the spectacle temples will be tilted from that perpendicular plane and unless the angle of tilt is properly measures, and an unprescribed cylinder will be created in the dispensed glasses.

Prior attempts to measure vertex distance have involved either complex devices such as the Wesseley Keratometer which itself uses another lens, a scale, and sighting pinhole and which must be altered for negative lenses, or simple devices wherein a disc with a stenopaic slit is inserted in the trial frame in place of the trial lens, and a millimeter ruler passed through the slit until it touches the closed eyelid. The complex instruments are relatively hard to use and expensive. The simple, slit type devices present problems of precision since the distance to the optical center of the trial lens and slit disc may differ since the various trial lenses have different amounts of curvature.

Various protractor type devices for measuring pantoscopic tilt have been deviced, but these devices are separate implements and require the refractionist to acquire two different devices to measure both vertex distance and pantoscopic tilt. Thus, it would be desirable to have one device which can both accurately measure both vertex distance and pantoscopic tilt.

SUMMARY OF THE INVENTION

The present invention is an ophthalmic measuring device for measuring the vertex distance between the optical centers of the anterior surface of the closed eyelid and the posterior spectacle surface of a trial lens mounted in a frame as well as the pantoscopic tilt angle at which the spectacle temples are moved off the frame front's perpendicular plane. This device is comprised of a generally planar member having a body portion, a measuring arm connected to the body portion, a second measuring arm, means slidably connecting the measuring arms and permitting relative movement therebetween. The measuring arms are disposed at an obtuse angle relative to the body portion. A measuring scale and indicating means are placed, one with respect to each of the measuring arms, whereby the vertex distance may be read directly from the scale and indicating means when the arms are moved to contact the optical centers of the anterior surface of the closed eyelid and the posterior trial lens surface, respectively. The device is further comprised of a pantoscopic tilt measuring means which is connected to the body portion, opposite to the extension of the measuring arms and in the same general plane as the measuring arms and body portion to add stability and in some modes of use, to act as a holder for the measuring device. The pantoscopic tilt measuring means is itself comprised of a flat edge perpendicular to the axis of the body portion, a sighting line perpendicular to the flat edge, and an arc measuring scale opposite from the flat edge which is intersected by the sighting line. Numerous other advantages and features of the present invention will become readily apparent from the following detailed description of the invention and of the one embodiment thereof, from the claims and from the accompanying drawings.

BRIEF DESCRIPTION OF THE DRAWINGS

In the accompanying drawings forming a part of the specification, and in which like numerals are employed to designate like parts throughout the same, FIG. 1 is a perspective view of the present invention shown adjacent to the patient's head measuring the vertex distance between the optical centers of the closed eyelid and the anterior surface of a lens mounted in a frame;

FIG. 2 is an enlarged plan view of the apparatus of the present invention shown in FIG. 1;

FIG. 3 is a fragmentary cross-sectional view taken along plane 3—3 of FIG. 2;

FIG. 4 is a cross-sectional view taken along plane 4—4 of FIG. 2.

DESCRIPTION OF THE PREFERRED EMBODIMENT

This invention may be used in many different forms. This specification and the accompanying drawings disclose only one specific form as an example of the use of the invention. The invention is not intended to be limited to the embodiment illustrated, and the scope of the invention will be pointed out in the appended claims. The precise shapes and sizes of the components herein described are not essential to the invention unless otherwise indicated, since the invention is described with only reference to an embodiment which is simple and straightforward.

The ophthalmic measuring device of the present invention is illustrated in FIG. 2 and is designated therein generally by numeral 10. This device is comprised of a first generally planar member 12 having a body portion defining a slot 14, and a measuring arm 16 connected to the planar body portion and disposed at an obtuse angle relative thereto. Superimposed on the planar member 12 is a second generally planar member 18 having two pins 20 connected thereto and extending into the slot 14 defined by the planar member 12. A second measuring arm 22 extends from the planar member 18 at an obtuse angle relative thereto and is disposed generally parallel to the first measuring arm 16. Movement of the member 18 is controlled by the pins 20 within the slot 14, by allowing limited movement of the arms 16 and 22 relative to each other. In the preferred embodiment, a third member 24 is connected to the pins 20 on the opposite side of the device from the member 18 and is disposed flush with the first generally planar member 12.

In the preferred embodiment of this invention, the tip 26 of the measuring arm 22 is rounded so that it may better contact the optical center of the posterior spectacle surface of a trial lens 28 mounted in a frame 30. The tip 32 of the measuring arm 16 is flattened and widened in the plane perpendicular to the general plane of the device to facilitate contact with the patient—s eyelid. The preferred embodiment also has a raised flange 36 connected to arm 16 which can contact the edge of arm 22, and which, along with the pins 20, serves to check the motion of the measuring arms relative to each other.

A further feature of the instant invention is a pantoscopic tilt measuring means 38 connected to the planar member 12 on the opposite side from the measuring arms 16 and 22 and in the same general plane as the first member 12. The pantoscopic tilt measuring means is comprised of a flat edge 40 perpendicular to the body portion of the planar member 12, a sighting line 42 perpendicular to the flat edge 40 and an arc measuring scale 44 opposite from the flat edge 40 which is intersected by the sighting line 42. The edge 46 of the pantoscopic tilt measuring means opposite to the perpendicular edge 40 is curved generally parallel to the arc measuring scale 44.

To measure the vertex distance with the present invention, the proper refraction for each eye is determined by the use of trial lenses 28 set into a frame 30 as is normally done in the art. The device is then placed along the patient's temple with the tip 32 of the first measuring arm 16 touching the optical center of the patient's closed eyelid 34. The second measuring arm 22 is then slid toward the posterior surface of the lens 28 mounted in the frame 30 until the tip 28 of the arm touches the optical center of the lens. FIG. 1 shows a perspective view of the present invention shown adjacent to a patient's head as described hereinabove.

The vertex distance measurement may be read off the scale 46 as indicated by the indicating means 48. The refractionist may make this measurement while the device is in place between the patient's eyelid and the lens, or to increase patient comfort, by holding the arms 16 and 22 in position, twisting the device to clear both eye and lens, extracting said device and then reading the distance.

I have found that such vertex distance measurements for the right eye may be quickly and easily taken by holding the curved edge 46 and the perpendicular edge 40 of the pantoscopic tilt measuring means with the right index finger and thumb, respectively; and sliding the second member with the left hand while adjusting the position of the device until contacts are made as hereinabove described. The device is simply turned over and the acts repeated for the left eye measurement. Operation of this device is not limited by the hereinabove right and left hand manipulations and the refractionist may find it more convenient to use one hand for the entire operation.

For one handed operation, the device is held by grasping the second and third members (18 and 24) with the thumb and index finger while exerting pressure on the first member (12) with the middle or third finger, thereby causing the measuring arms (16 and 22) to slide relative to each other. When used in this mode, the pantoscopic tilt measuring means 38 serves as a counterweight to the arms, thereby adding to the stability of the device.

Of course, the modes of operation described hereinabove are not intended to be the only possible modes of operation. In using this device, the refractionist may find that combinations of the above modes or an entirely different mode of operation may be more convenient.

In the preferred embodiment of the invention, the vertex measuring scale 46 is marked in millimeter increments, and the scale is corrected for the thickness of the human eyelid.

To measure pantoscopic tilt, the frame 30 is held horizontally with the trial frame temple (not shown) to be measured fully extended. The perpendicular edge 40 is rested along the spectacle trial lens plane, and the sighting line 42 is placed adjacent to the center barrel of the frame hinge (not shown). The degrees of tilt can then be easily read off the arc measuring scale 44, which in the preferred embodiment is marked in degrees of arc. The same method may be employed for measuring tilt for each trial frame temple.

The ophthalmic measuring device of this invention may be manufactured from wood, metal, plastic, hard rubber or any other material or composite which will meet the minimal structural requirements needed of any measuring instrument. In the preferred embodiment, the device is constructed from a hard plastic.

The above detailed description has been given for ease of understanding only. No unnecessary limitations are to be understood therefrom, as modifications will be obvious to those skilled in the art.

I claim:

1. An ophthalmic measuring device for determining the vertex distance between the optical centers of the anterior surfaceof the closed eyelid and the posterior spectacle surface of a trial lens mounted in a frame, which device is comprised of a generally planar member having a body portion, a measuring arm connected to said body portion, a second measuring arm, one of said arms including an eyelid contacting tip for engaging the optical center of the closed eyelid, said eyelid contacting tip being flattened and widened in the plane perpendicular to the general plane of said device and the other of said arms including a rounded trial lens contacting tip for engaging the optical center of the posterior spectacle surface, means slidably connecting said measuring arms and permitting relative movement therebetween, said arms being disposed at an obtuse angle relative to said body portion, and a measuring scale and indicating means placed, one with respect to each of said arms, whereby the vertex distance may be read directly from said scale and indicating means when said arms are moved to contact the optical centers of the anterior surface of the closed eyelid and the posterior lens surface, respectively.

2. An ophthalmic measuring device including a first generally planar member having a body portion defining a slot and a first measuring arm extending from said body portion, a second member superimposed on said first member and having a body portion including a pin extending into the slot of said first member, said second member having a second measuring arm extending therefrom and disposed generally parallel to said first arm, whereby movement of said second member relative to said first member will move the arms relative to each other, the body portions of said first and second members defining cooperating measuring means to indicate the distance between said arms when used to measure the distance between the optical centers of the anterior surface of the closed eyelid and the posterior spectacle lens surface, and a pantoscopic tilt measuring means secured to one of said body members for measuring the pantoscopic tilt angle at which the spectacle temples are moved off the frame front's perpendicular plane.

3. An ophthalmic measuring device for determining the vertex distance between the optical centers of the anterior surface of the closed eyelid and the posterior spectacle surface of a trial lens mounted in a frame, which device is comprised of a generally planar member having a body portion, a measuring arm connected to said body portion, a second measuring arm, means slidably connecting said measuring arms and permitting relative movement therebetween, said arms being disposed at an obtuse angle relative to said body portion, a measuring scale and indicating means placed, one with respect to each of said arms, whereby the vertex distance may be read directly from said scale and indicating means when said arms are moved to contact the optical centers of the anterior surface of the closed eyelid and the posterior lens surface, respectively, and a means for measuring the pantoscopic tilt angle at which the spectacle temples are moved off the frame front's perpendicular plane, which pantoscopic tilt measuring means is connected to said body portion, opposite to the extension of said measuring arms and in the same general plane as said measuring arms and body portion to add stability to said measuring device.

4. An ophthalmic measuring device as defined in claim 3, wherein said pantoscopic tile measuring means is comprised of a flat edge perpendicular to the axis of said body portion, a sighting line perpendicular to said flat edge, and an arc measuring scale opposite from said flat edge which is intersected by said sighting line.

5. An ophthalmic measuring device as defined in claim 4, wherein the vertex distance measuring scale is on the pantoscopic tilt measuring means and the indicating means for said scale is on the measuring arm which slides relative to said pantoscopic tilt measuring means.

* * * * *